United States Patent [19]

Aono et al.

[11] 4,183,859
[45] Jan. 15, 1980

[54] THENOYLINDAN DERIVATIVES

[75] Inventors: Tetsuya Aono, Kyoto; Yasuhiko Kawano, Suita, both of Japan

[73] Assignee: Takeda Chemical Industries, Ltd., Osaka, Japan

[21] Appl. No.: 893,303

[22] Filed: Apr. 4, 1978

[30] Foreign Application Priority Data

Apr. 6, 1977 [JP] Japan .................................. 52-39792

[51] Int. Cl.² .................. C07D 333/24; C07D 333/16; A01N 9/00
[52] U.S. Cl. ...................................... 549/72; 424/275
[58] Field of Search .................. 260/332.2 A, 332.3 C

[56] References Cited

U.S. PATENT DOCUMENTS 3,953,500  4/1976  Noguchi et al. ...................... 260/517

OTHER PUBLICATIONS

Kirsch et al., Liebigs Ann. Chem., (1976), pp. 1914-1924.

Primary Examiner—Alan Siegel
Attorney, Agent, or Firm—Wenderoth, Lind & Ponack

[57] ABSTRACT

Compounds of formula:

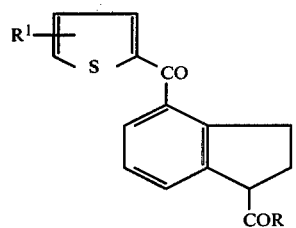

wherein R is hydroxyl, lower alkoxy having 1 to 4 carbon atoms or amino and $R^1$ is hydrogen or lower alkyl having 1 to 4 carbon atoms, are useful as medicines such as antipyretics, analgesics and antiinflammatory agents.

5 Claims, No Drawings

THENOYLINDAN DERIVATIVES

This invention relates to novel indan derivatives which are of value as antipyretics, analgesics, antiinflammatory agents and other medicaments. More particularly, the invention relates to thenoylindan derivatives of the general formula:

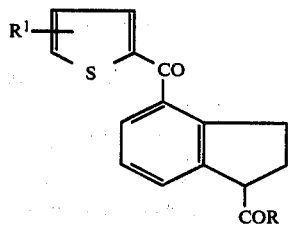
[I]

[wherein R is hydroxyl, lower alkoxy having 1 to 4 carbon atoms or amino; $R^1$ is hydrogen or lower alkyl having 1 to 4 carbon atoms]

Referrring to the above general formula [I], the lower alkoxy represented by R is, for example, methoxy, ethoxy, propoxy, isopropoxy, butoxy, isobutoxy, etc. The lower alkyl represented by $R^1$ is, for example, methyl, ethyl, propyl, isopropyl, butyl, etc. $R^1$ may be located in any optional position on the thiophene ring.

The following is a partial listing of compounds according to this invention.
(1) 4-(2-thienylcarbonyl)-1-indancarboxylic acid
(2) 4-(2-thienylcarbonyl)-1-indancarboxamide
(3) methyl 4-(2-thienylcarbonyl)-1-indancarboxylate
(4) 4-(5-methyl-2-thienylcarbonyl)-1-indancarboxylic acid
(5) 4-(4-methyl-2-thienylcarbonyl)-1-indancarboxylic acid The compounds [I] according to this invention show antiinflammatory, analgesic and antipyretic actions in human beings and animals such as rats and mice. For example, those compounds exhibit antiinflammatory activity at a dose level of 0.75 mg/kg or more against carrageenin edema on the hind leg of rats, and analgesic activity at a dose level of 0.39 mg/kg or more against phenylquinone writhing in mice.

For use as medicines, the contemplated compounds of this invention may be orally administered at a usual dose level of about 10 to 1000 mg daily per adult human, either as such or in the various dosage forms of tablets, capsules, granules, liquids, etc. as formulated with pharmacologically acceptable inert carriers. The compounds may also be administered by other routes, in the various dosage forms of injections, ointments, suppositories, etc. as formulated with pharmacologically acceptable inert carriers. In the latter instances, the dose level may range from about 5 mg to about 500 mg daily per adult human.

The indan derivatives [I] of this invention are all novel compounds and may for example be produced as follows. Thus, [Step I] a compound of the general formula:

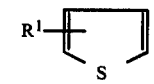
[II]

or a reactive derivative thereof with respect to the carboxyl function is reacted with a compound of the general formula:

$R^1 —\boxed{\phantom{X}}— S$
[III]

[wherein $R^1$ has the meaning defined hereinbefore] to obtain a compound of the general formula:

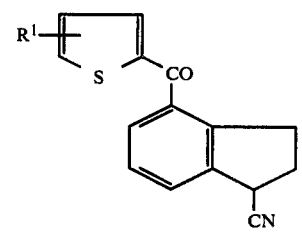
[IV]

[wherein $R^1$ has the meaning defined hereinbefore] and, then, [Step 2] the compound [IV] is solvolyzed to obtain an indan derivative of general formula [I].

This production method will hereinafter be described in detail.

In Step I, compound [II] may be used as such or after it has been converted to a reactive derivative thereof with respect to the carboxyl function. Generally, the reaction can be conducted with added facility when such a reactive derivative is employed. As examples of said reactive derivative, the acid anhydride and acid halides (e.g. acid chloride, acid bromide, etc.) may be mentioned. Generally the reaction may be conducted with advantage in the presence of a catalyst and a solvent. Normally the catalyst is one that is employed in Friedel-Crafts reactions. Typical examples of such catalyst are metal halides (e.g. aluminum chloride, aluminum bromide, iron chloride, iron bromide, tin chloride, tin bromide, zinc chloride, zinc bromide, anitmony chloride, antimony bromide, etc.). While the solvent may be any solvent inert to the reaction, carbon disulfide, methylene chloride, chloroform, carbon tetrachloride, ethylene chloride, tetrachloroethane, etc. are particularly preferred for commercial purposes. The reaction may also be carried out using an increased proportion of starting compound [III] in lieu of using the solvent. The proportion of the catalyst may be about 1 to 1.5 mol equivalents, preferably about 1 to 1.1 mol equivalents with respect to each mol of carboxylic acid [II] or a reactive derivative thereof. The reaction may be conducted under cooling or heating, i.e. at a suitable temperature from −20° C. to the boiling point of the solvent used, preferably between −15° C. and +50° C.

While the reaction time varies with the catalyst or/and solvent used, it is normally in the range of 0.5 to 30 hours. The resultant compound of general formula [IV] can be separated and purified by procedures known per se, such as distillation, column chromatography and so on.

The solvolysis of Step 2 may for example be hydrolysis with water or alcoholysis with an alcohol. The solvolysis is advantageously carried out in the presence of a catalyst. As said catalyst, there may be mentioned hydrogen halides (e.g. hydrogen chloride, hydrogen bromide, hydrogen iodide, etc.), mineral acids such as sulfuric acid, phosphoric acid, polyphosphoric acid, etc.; organic acids such as formic acid, acetic acid, p-toluenesulfonic acid, etc.; Lewis acids such as boron trifluoride, titanium tetrachloride, etc.; and alkali metal hydroxides such as sodium hydroxide, potassium hydroxide, etc. Those catalysts may be employed either alone or in a combination of two or more. Generally the reaction may be conducted under cooling, at room temperature or under heating, the proper temperature being selected from the range of 0° to 200° C. as it is the case with ordinary solvolysis reactions. While there is no particular limitation on the reaction time, the reaction is normally conducted for 0.5 to 70 hours.

When the above solvolysis reaction of compound [IV] is effected with an alcohol, the compound [I] is obtained in the form of an ester with R corresponding to the alcohol employed. Solvolysis of compound [IV] by means of water yields, under mild conditions, the compound [I] in which R is an amino group and, under severe conditions, the compound [I] wherein R is a hydroxyl group as the amide is further hydrolyzed. In the latter instance, it is, of course, possible to isolate the amide and carry out the hydrolysis further until the free carboxylic acid is obtained. For example, the amide is obtained when sulfuric acid, for instance, is employed as the catalyst when cold, when polyphosphoric acid is employed as the catalyst when hot or when boron trifluoride is employed at room temperature. When sulfuric acid, an alkali metal hydroxide or a hydrogen halide is employed when hot, there is obtained the carboxylic acid wherein R is hydroxyl.

The resultant compound [I] may, if desired, be interconverted by procedures known per se, i.e. among compounds wherein Rs are hydroxyl, alkoxy and amino, respectively.

As methods for converting the free carboxylic acid to the amide derivative, amidation by reaction with an amine or amidation by reaction with an amine after conversion to the acid chloride may be mentioned by way of example. The conversion of the free carboxylic acid to an ester derivative may be effected, for example by reaction with an alcohol in the presence of acid.

The conversions of acid amide derivative to ester derivative may be accomplished, for example by alcoholysis using an acid as the catalyst.

The conversion of such ester derivative to free carboxylic acid may be accomplished, for example by hydrolysis in the presence of alkali or acid.

The conversion of ester derivative to acid amide derivative may be effected by amidation which comprises reacting the ester with an amine.

The resultant compound [I] of this invention can be purified by routine separatory procedures such as recrystallization, distillation, chromatography, etc.

The compound [I] according to this invention contains an asymmetric carbon atom in 1-position and, as such, may be resolved into optical isomers, i.e. the dextro- and levo- forms. Thus, the racemic free acid is added to a suitable inert solvent such as chloroform, acetone, benzene, hexane, ether, methanol, ethanol, acetonitrile or water and reacted with an optically active base. The resultant salt or amide is separated into diastereoisomers by utilizing their differential solubilities. Thereafter, the optically active free carboxylic acid derivatives are obtained by treatment with an acid. As an alternative, the racemic free acid is reacted with a suitable optically active alcohol to prepare an ester which is then separated into diastereoisomers by means conventional per se, e.g. recrystallization, distillation, chromatorgraphy, etc. The ester is then hydrolyzed in the presence of an acid or a base. In this manner, too, the optically active free carboxylic acids can be isolated. The optically active base thus employed may for example be an amine such as quinine, brucine, cinchonidine, cinchonine, dehydroabietylamine, hydroxyhydrinamine, methylamine, morphine, α-phenylethylamine, phenyloxynaphthylamine, quinidine, strychnine, or the like, a basic amino acid such as lysine, arginine or the like, and an amino acid ester. The optically active alcohol may for example be borneol, menthol, 2-octanol or the like. The compound of general formula [I] obtained by the aforementioned optical resolution can be converted to optically active derivatives with respect to the carboxyl function by the aforementioned procedures known per se.

REFERENCE EXAMPLE 1

To 2.5 g of 1-cyano-4-indancarboxylic acid is added 40 ml of chloroform together with 25 g of thionyl chloride and the mixture is stirred at room temperature overnight. The chloroform and excess thionyl chloride are distilled off under reduced pressure at about 30° C. To the residue is added about 50 ml of carbon tetrachloride, followed by distillation under reduced pressure; this process is repeated 4 times. The acid chloride is obtained as the residue.

To 15 ml of methylene chloride is added 1.15 g of thiophene and while the mixture is stirred at $-15°$ C., 3.5 g of tin tetrachloride is added. Then, a solution of the above acid chloride in 10 ml of methylene chloride is added dropwise. During the dropwise addition, the reaction temperature is controlled below $-10°$ C. After the dropwise addition has been completed, the mixture is stirred at $-10 \sim -15°$ C. for 1.5 hours and at room temperature for one hour. After decomposition of the complex by the addition of ice-hydrochloric acid, the mixture is extracted with methylene chloride. The extract is washed with water and dried, and the solvent is distilled off under reduced pressure. The residue is purified by column chromatography (250 g silica gel; elution with benzene-ethyl acetate = 100:1). By the above procedure is obtained 4-(2-thienylcarbonyl)-1-indancarbonitrile as an oil.

Infrared absorption spectrum:
2230 cm$^{-1}$, absorption assignable to the nitrile group
1630 cm$^{-1}$, absorption assignable to the carbonyl group

EXAMPLE 1

To 2.5 g of 4-(2-thienylcarbonyl)-1-indancarbonitrile is added 20 ml of 60% sulfuric acid together with 10 ml of acetic acid. The mixture is refluxed in argon gas for 2.5 hours. After cooling, water is added to the reaction mixture which is then extracted with benzene. The benzene layer is washed with water and extracted with a 5% aqueous solution of potassium carbonate. The extract is made acidic with hydrochloric acid and the precipitate is extracted with benzene. The benzene layer is washed with water, dried and decolorized with activated carbon. The solvent is then distilled off under reduced pressure and the residue is crystallized from benzene-cyclohexane (1:2). By the above procedure is obtained 4-(2-thienylcarbonyl)-1-indancarboxylic acid as crystals melting at 121.5°–123.5° C.

Elemental analysis, for $C_{15}H_{12}O_3S$; Calcd. C, 66.15; H, 4.44; Found C, 66.36; H, 4.40.

EXAMPLE 2

In 50 ml of dry methanol is dissolved 3.0 g of 4-(2-thienylcarbonyl)-1-indancarbonitrile, and hydrogen chloride gas is bubbled into the solution. After a sufficient amount of hydrogen chloride has been absorbed, the mixture is allowed to stand at room temperature overnight. The methanol is distilled off under reduced pressure and the residue is diluted with water and extracted with benzene. The extract is washed with water and dried, and the solvent is distilled off under reduced pressure. The residue is purified by column chromatography (silica gel; eluant: benzene-ethyl acetate=95:5). By the above procedure is obtained methyl 4-(2-thienylcarbonyl)-1-indan-carboxylate as an oil.

Elemental analysis, for $C_{16}H_{14}O_3S$; Calcd. C, 67.12; H, 4.93; Found C, 67.38; H, 5.02.

Infrared absorption spectrum:
1720 $cm^{-1}$: ester
1640 $cm^{-1}$: ketone

EXAMPLE 3

To 2.5 g of 4-(2-thienylcarbonyl)-1-indancarbonitrile is added 50 g of polyphosphoric acid and, with occasional stirring, the mixture is heated at 80° C. for 2.5 hours. The polyphosphoric acid is decomposed by the addition of water, followed by extraction with ethyl acetate. The extract is washed with water and dried. The solvent is distilled off under reduced pressure and the residue obtained is recrystallized from ethyl acetate. By the above procedure is obtained 4-(2-thienylcarbonyl)-1-indancarboxamide as crystals melting at 164°–166° C.

Elemental analysis, for $C_{15}H_{13}NO_2S$ Calcd. C, 66.41; H, 4.83; N, 5.16; Found C, 66.27; H, 4.79; N, 5.07.

What is claimed is:

1. A compound of the formula:

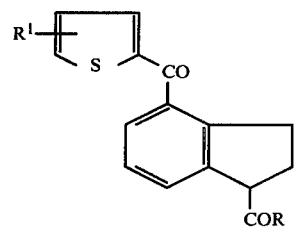

wherein R is hydroxyl, amino or a lower alkyl having 1 to 4 carbon atoms and $R^1$ is hydrogen or a lower alkyl having 1 to 4 carbon atoms.

2. A compound as claimed in claim 1, wherein $R^1$ is hydrogen.

3. A compound as claimed in claim 1, wherein the compound is 4-(2-thienylcarbonyl)-1-indancarboxylic acid.

4. A compound as claimed in claim 1, wherein the compound is methyl 4-(2-thienylcarbonyl)-1-indancarboxylate.

5. A compound as claimed in claim 1, wherein the compound is 4-(2-thienylcarbonyl)-1-indancarboxamide.

* * * * *